United States Patent
Aitken et al.

(10) Patent No.: US 11,485,992 B2
(45) Date of Patent: Nov. 1, 2022

(54) SCREENING AND CULTURE METHOD

(71) Applicant: OTAKARO PATHWAYS LIMITED, Christchurch (NZ)

(72) Inventors: John Milford Aitken, Christchurch (NZ); Kevin Andrew Taylor, Christchurch (NZ)

(73) Assignee: OTAKARO PATHWAYS LIMITED

( * ) Notice: Subject to any disclaimer, the term of this patent is extended or adjusted under 35 U.S.C. 154(b) by 219 days.

(21) Appl. No.: 15/780,247

(22) PCT Filed: Dec. 14, 2016

(86) PCT No.: PCT/IB2016/057595
§ 371 (c)(1),
(2) Date: May 31, 2018

(87) PCT Pub. No.: WO2017/103799
PCT Pub. Date: Jun. 22, 2017

(65) Prior Publication Data
US 2019/0144911 A1    May 16, 2019

(30) Foreign Application Priority Data

Dec. 14, 2015 (NZ) .......................... 711052
Mar. 11, 2016 (NZ) .......................... 717913

(51) Int. Cl.
*C12Q 1/04* (2006.01)
*G01N 1/20* (2006.01)
(Continued)

(52) U.S. Cl.
CPC ............. *C12Q 1/045* (2013.01); *C12N 1/20* (2013.01); *C12Q 1/025* (2013.01); *C12Q 1/04* (2013.01); *C12Q 1/06* (2013.01); *G01N 1/20* (2013.01); *G01N 1/30* (2013.01); *G01N 2333/35* (2013.01); *G01N 2800/065* (2013.01)

(58) Field of Classification Search
CPC . C12Q 1/045; C12Q 1/04; C12Q 1/06; C12Q 1/025; C12N 1/20; G01N 1/30; G01N 1/20; G01N 2800/065; G01N 2333/35
See application file for complete search history.

(56) References Cited

U.S. PATENT DOCUMENTS 7,488,580 B1 * 2/2009 Naser .................. C12Q 1/689
  435/6.16
2015/0064703 A1 * 3/2015 Super ............... G01N 33/56911
  435/6.12

OTHER PUBLICATIONS

Dhurat, R. et al., Principles and Methods of Preparation of Platelet-Rich Plasma: A Review and Author's Perspective, 2014, Journal of Cutaneous and Aesthetic Surgery, 7(4), 189-197 (Year: 2014).*

(Continued)

*Primary Examiner* — Louise W Humphrey
*Assistant Examiner* — Anjali Ajit Hirani
(74) *Attorney, Agent, or Firm* — Galbreath Law Offices, P.C.; John A. Galbreath

(57) ABSTRACT

Methods of culturing and detecting a biomarker which may be associated with autoimmune diseases, in particular inflammatory bowel disease and Crohn's disease; also a screening method for substances suitable for the treatment of inflammatory bowel disease including Crohn's disease; the method including culturing a biomarker in a culture media which includes a culture broth, OADC, PANTA and Myco-bactin J.

23 Claims, 5 Drawing Sheets

(51) Int. Cl.
*G01N 1/30* (2006.01)
*C12N 1/20* (2006.01)
*C12Q 1/02* (2006.01)
*C12Q 1/06* (2006.01)

(56) References Cited

OTHER PUBLICATIONS

Aung, K. J. M. et al., Hydrochloric vs. sulphuric acid in water for Ziehl-Neelsen staining of acid-fast bacilli, 2011, The International Journal of Tuberculosis and Lung Disease, 15(7), 955-958 (Year: 2011).*

Carniel, F., Use of conventional PCR and smear microscopy to diagnose pulmonary tuberculosis in the Amazonian rainforest area, 2014, Brazilian Journal of Medical and Biological Research, 47(12), 1016-1020 (Year: 2014).*

Holland, K. et al., A Procedure for Selecting and Isolating Specific Auxotrophic Mutants of *Mycobacterium smegmatis*, 1971, Journal of General Microbiology, 66, 115-118 (Year: 1971).*

Schwartz, D. et al., Use of short-term culture for identification of *Mycobacterium avium* subsp. *Paratuberculosis* in tissue from Crohn's disease patients, 2000, Clinical Microbiology and Infectious Diseases, 6, 303-307 (Year: 2000).*

Selvakumar, N. et al., "Inefficiency of 0.3% carbol fuchsin in Ziehl-Neelsen staining for detecting acid-fast bacilli", Journal of Clinical Microbiology. 2002, vol. 40, pp. 3041-3043.

Aung, K.J.M. et al., "Hydrochloric vs. sulphuric acid in water for Ziehl-Neelsen staining of acid-fast bacilli", The International Journal of Tuberculosis and Lung Disease. 2011, vol. 15, pp. 955-958.

Nyka, W. "Studies on *Mycobacterium tuberculosis* in lesions of the human lung", American Review of Respiratory Disease. 1963, vol. 88, pp. 670-679.

Gearrey, R.B. et al., "Gastrointestinal: *Mycobacterium avium* ssp. *paratuberculosis* and Crohn's disease", Journal of Gastroenterolgy and Hepatology. 2005, vol. 20, p. 1943.

Markesich, D.C. et al., "Progress in culture and subculture of spheroplasts and fastidious acid-fast bacilli isolated from intestinal tissues", Journal of Clinical Microbiology. 1988, vol. 26, pp. 1600-1603.

Schwartz, D. et al., "Use of short-term culture for identification of *Mycobacterium avium* subsp. *paratuberculosis* in tissues from Crohn's patients", Clinical Microbiology and Infection. 2000, vol. 6, pp. 303-307.

Naser, S.A. et al., "Culture of *Mycobacterium avium* subspecies *paratuberculosis* from the blood of patients with Crohn's disease", Lancet. 2004, vol. 364, pp. 10391044.

Banche, G. et al., "Application of multiple laboratory tests for *Mycobacterium avium* ssp. *paratuberculosis* detection in Crohn's disease patient specimens", New Microbiologica. 2015, vol. 38, pp. 357-367.

Giuliana Banche et al., "Application of multiple laboratory tests for *Mycobacterium avium* ssp. *paratuberculosis* detection in Crohn's disease patient specimens", New Microbiologica, 2015, vol. 38, pp. 357-367.

Catherine Vilchèze et al., "Acid-Fast Positive and Acid-Fast Negative *Mycobacterium tuberculosis*: The Koch Paradox", published Mar. 24, 2017, pp. 1-14.

* cited by examiner

SCREENING AND CULTURE METHOD

TECHNICAL FIELD

The present invention relates to methods of culturing and detecting a biomarker that may be associated with autoimmune diseases, in particular inflammatory bowel disease, especially Crohn's disease. Another aspect of the present invention relates to the provision of a screening method for substances suitable for the treatment and/or prevention of inflammatory bowel disease, in particular Crohn's Disease.

BACKGROUND ART

Any discussion of the prior art throughout the specification is not an admission that such prior art is widely known or forms part of the common general knowledge in the field.

Crohn's disease (CD) is a type of inflammatory bowel disease (IBD), affecting the gastrointestinal tract, and causing inter alia abdominal pain, diarrhea, fever, and weight loss. Current diagnosis techniques for CD include colonoscopy, radiologic tests, and blood tests; these tests are often invasive, unreliable, and a combination of tests is often required. As such, CD can be difficult to diagnose.

Uncovering the cause of inflammatory bowel disease appears to have become the holy grail of gastroenterology. For CD the most popular hypothesis is that the disease results from loss of immunological tolerance to bacteria or other microorganisms that are normally present in the bowel lumen. However, several other hypotheses exist including a role for infectious agents such as atypical mycobacteria, *Chlamydia* species, *Listeria monocytogenes*, cell wall deficient *Pseudomonas* species, *Mycoplasma* species and a number of viruses including measles virus. The debate on the cause of CD remains unresolved.

Johne's disease (JD), a disease that primarily affects the small intestine of ruminants, is caused by *Mycobacterium avium* subspecies paratuberculosis (MAP). Due to similarities between JD and CD a link between MAP and CD has been posited in recent years.

Culturing MAP from ruminants suffering from JD is a standard procedure, but a method of culturing and identifying MAP from humans suffering from CD in such a way that is replicatable and reliable has been elusive. Researchers have relied upon identification of MAP in CD patients by detecting the MAP-specific insertion element IS900 by PCR. However, several researchers now believe that the IS900 insertion element is not a reliable marker for either MAP in humans or for reliable diagnosis of CD.

In 2000, Schwartz et al. described a short-term culture for identification of MAP from tissue of human CD patients. The culture medium was a standard Mycobacterial growth Indicator Tube (MGIT) and 12B* Bactec bottle (Becton Dickinson, Franklin Lake, N.J., USA): 7H9-broth base supplemented with OADC, mycobactin J, and PANTA antibiotics mixture, the MGIT tube also supplemented with L-asparagine, pyroxidine, trace elements, biotin, and glycerol. Staining of a sample of the cultured sample was carried out with Kinyoun acid-fast stain as previously published (Nyka W. Method for staining both acid-fast and chromophobic tubercle bacilli with carbolfuchsin. J Bacteriol 1967; 93:1458-60). Two forms of MAP were visualised using this method: a prespheroplast form with a partial cell wall compartment, and a *bacillus* intact cell form.

In a 2004 study, Naser et al. described culture of MAP in the same culture media as the Schwartz et al. study from peripheral blood samples from human CD patients. Again, acid-fast bacilli and prespheroplasts were observed after 12 weeks of incubation in cultures identified as being MAP-positive by IS900-nested PCR analysis. No organisms were detectable by acid-fast Ziehl-Neelsen (ZN) staining in the early weeks of culture. Furthermore, viable MAP was only cultured from 50% of CD patients.

Neither Schwartz's nor Naser's methods have proven reliably replicatable so as to be relied upon for diagnosis of CD or inflammatory bowel disease.

In 2005 the Applicant attempted to replicate the findings from the Naser et al. study. Using a modified technique, the Applicant identified round "inclusions" within the cytoplasm of macrophages of patients with active CD (*Journal of Gastroenterology and Hepatology* (2005) 20, 1943). ZN staining (using alcohol-free de-colouriser) showed these "inclusions" as "red spots."

At the time the Applicant believed the "red spots" to be spheroplastic phase forms of MAP (i.e. cell wall-deficient), due to the presence of the IS900 marker in the CD patient samples. However, IS900 as a marker for MAP now has a number of detractors, and IS900 is now not considered to be a reliable marker for the presence of the macrophage inclusions in CD patients. The number of copies of IS900 is lower in the macrophage inclusions than in bovine strains, and a positive PCR result for IS900 does not indicate a viable strain, or active growth, of MAP, as dead bacilli of DNA remnants thereof will also generate a positive PCR result. Published data shows positive results for IS900 in only 40-70% of CD patients, as well as positive results in controls. Thus, the presence or absence of IS900 is not a reliable diagnostic test for CD. It is possible the "inclusions" were MAP-like organisms, not MAP.

Spheroplastic forms of the identified organism have proven difficult to cultivate. Accordingly, the Applicant has conducted subsequent research directed at the application of bacteriological methodologies for reliable subculture and identification of the macrophage 'inclusions'.

It is an object of the present invention to overcome or mitigate at least some of the difficulties identified above. Another object of the present invention is to provide a more reliable method of culture and identification of the previously identified 'inclusions', and a further object of the invention is to provide a method of diagnosis of IBD or CD on the basis of identification of said inclusions.

The Applicant does not assert that the biomarker cultured and detected by the method of the present invention is the cause of any autoimmune disease, but simply that the presence of the biomarker can be used as a reliable indication of the presence of an autoimmune disease, in particular inflammatory bowel disease and especially Crohn's Disease.

It is thought that the biomarker cultured and detected by the method of the present invention may be a *Mycobacterium* species (as yet unidentified) which has been found to be strongly associated with the occurrence of CD; it is not yet established whether this biomarker is in fact a causative agent of CD.

However, it is possible, but not yet proved, that the biomarker detected by the method of the present invention is in fact *Mycobacterium avium* subspecies paratuberculosis (MAP) or a MAP-like organism; it is also possible that this organism is actually the cause of inflammatory bowel disease or Crohn's disease rather than simply a biomarker.

DISCLOSURE OF INVENTION

The present invention provides a method for cultivating a biomarker, said method including the steps of culturing a patient sample in culture media selective for mycobacteria, wherein said culture media includes:
- a culture broth (as herein defined);
- OADC (as herein defined);
- PANTA (as herein defined);
- Mycobactin J.

Preferably, said culture medium further includes filtered 100% disaccharide solution.

Preferably, the culture medium includes:
- a culture broth in the form of 7H9 broth prepared in accordance with the manufacturer's instructions;
- a vial of PANTA as supplied by the manufacturers dissolved in 15 millilitres of OADC, with the resulting solution added to approximately 900 millilitres of 7H9 broth;
- mycobactin J added to the culture broth in a proportion of 0.05 millilitres to 10 millilitres of broth;
- 0.2 millilitres of disaccharide solution for every 10 millilitres of broth.

The present invention further provides a method of culturing and staining a biomarker, said method including the step of culturing a patient sample as described above, and further including step of staining said cultured sample using Ziehl-Neelsen stain, wherein said Ziehl-Neelsen staining method does not use alcohol in the decolouriser. Preferably the stain is Kinyoun carbol fuchsin. Preferably the counterstain is methylene blue, and most preferably 1% methylene blue in distilled $H_2O$. Preferably the decolouriser is $H_2SO_4$, more preferably 20% $H_2SO_4$.

Preferably the patient sample is a peripheral blood sample. Preferably the peripheral blood sample is collected using sodium citrate as an anticoagulant.

Preferably the biomarker is indicative of inflammatory bowel disease, more preferably the biomarker is indicative of Crohn's Disease.

Preferably the method includes:
- a culturing step, as previously described;
- after a first predetermined period of time a first sample is taken from the culture and subjected to the staining step, as described above, and the number of spheroplastic forms of the biomarker is counted;
- after a second predetermined period of time a second sample is taken from the culture and subjected to the staining step, as described above, and the number of spheroplastic forms of the biomarker is counted; and
- the number of spheroplastic forms of the biomarker in the first sample reading and the second sample reading is compared.

Preferably, the method further includes a diagnosis step, wherein active inflammatory bowel disease, preferably Crohn's Disease, is diagnosed on the basis of an increase in the number of spheroplastic forms and the morphology of the biomarker.

However, it is emphasised that for a conclusive diagnosis of inflammatory bowel disease or Crohn's disease, the diagnosis step described in this specification would need to be supplemented by a biopsy of the affected region of the bowel, possibly with the addition of MRI scans as well. The diagnosis method of the present invention offers an inexpensive and non-invasive option for preliminary diagnosis and/or for comparing possible treatments for inflammatory bowel disease or Crohn's disease.

The second predetermined period of time is longer than the first predetermined period of time such that the multiplication of the biomarker is allowed to occur. The Applicant has found that a first predetermined period of time of 8 days after the culture media has been inoculated by the patient sample, and a second predetermined period of time is 30 days after the culture media has been inoculated by the patient sample, is sufficient to allow this multiplication to occur. However, these periods may be varied at the discretion of the person conducting the investigation, and more samples may be taken if necessary.

The present invention further provides a method for determining the efficacy of treatment of inflammatory bowel disease, preferably Crohn's Disease, wherein said method includes:
- a first culturing step, wherein a first patient sample is provided by a patient before treatment for inflammatory bowel disease and subjected to the culturing step as described above;
- after a predetermined period of time a first sample is taken from the culture and subjected to the staining step, as described above, and the number of spheroplastic forms of biomarker counted;
- a second culturing step, wherein a second patient sample is provided by the patient during or after treatment for inflammatory bowel disease and subjected to the culturing step as described above;
- after a predetermined period of time a second sample is taken from the culture and subjected to the staining step, as described above, and the number of spheroplastic forms of the biomarker counted; and
- the number of spheroplastic forms and morphology of the biomarker in the first sample and the second sample are compared.

Preferably, the first sample and second sample are each stained after both a first predetermined period and a second predetermined period, most preferably 8 days and 30 days from culture respectively. Preferably, the method further includes a determining step, wherein said treatment for inflammatory bowel disease, preferably Crohn's Disease, is deemed efficacious if the number of spheroplastic forms of the biomarker in the second sample is significantly lower than the first sample.

The present invention also provides a screening method for assessing substances in relation to a biomarker, said method including the steps:
a. taking a sample of peripheral blood from a patient;
b. culturing a plurality of sub samples of said sample, using the above method;
c. wherein at least one sub sample is a control and each of the remaining sub samples has a substance to be assessed added to it before culturing;
d. wherein culturing includes incubating all of the sub samples at a predetermined temperature for a first period;
e. sampling the contents of each sub sample and staining this sample using Ziehl-Neelsen method staining wherein the decolouriser used in said staining method does not use or include alcohol;
f. counting and recording the incidence of red spots in each sample;
g. re-incubating all said sub samples at said predetermined temperature for a second period;
h. repeating steps e and f;
i. comparing the results of step f for each sub sample after said first and second periods.

BRIEF DESCRIPTION OF DRAWINGS

By way of example only, preferred embodiments of the present invention are described in detail below with reference to the accompanying drawings, in which.

BEST MODE FOR CARRYING OUT THE INVENTION

Definitions

The term "red spots", "inclusions", "L forms of Mycobacterium species" (or "LFB") and "spheroplastic form of the organism" (and variations thereof), are used interchangeably, and refer to the microscopic organisms identified in the Applicant's technique.

"Culture broth" includes any nutrient broth including 7H9, 7H11, Columbia, MGIT (Becton, Dickinson).

"Supplementation" includes any amino acid, sugar, antibiotic, or commercially available supplement (e.g. OADC, PANTA).

"Stain", unless otherwise indicated, includes the conventional ZN staining method described by CDC, in the alcohol-free variant described below.

Mycobactin J is a proprietary preparation of ferric mycobactin; it is an ion-chelated compound and is used as a growth supplement at the culturing stage of MAP.

According to the present invention, the Applicant has, for the first time, been able to reliably and clearly visualise spheroplastic forms of an un-identified organism in peripheral blood samples from patients suffering from Crohn's Disease. In the preferred embodiment of the invention, the spheroplastic forms of the un-identified organism, also referred to as a biomarker or "red spot", is first induced by incubation in a specific culture broth and subsequently detected by the use of acid-fast staining.

Figure 1:
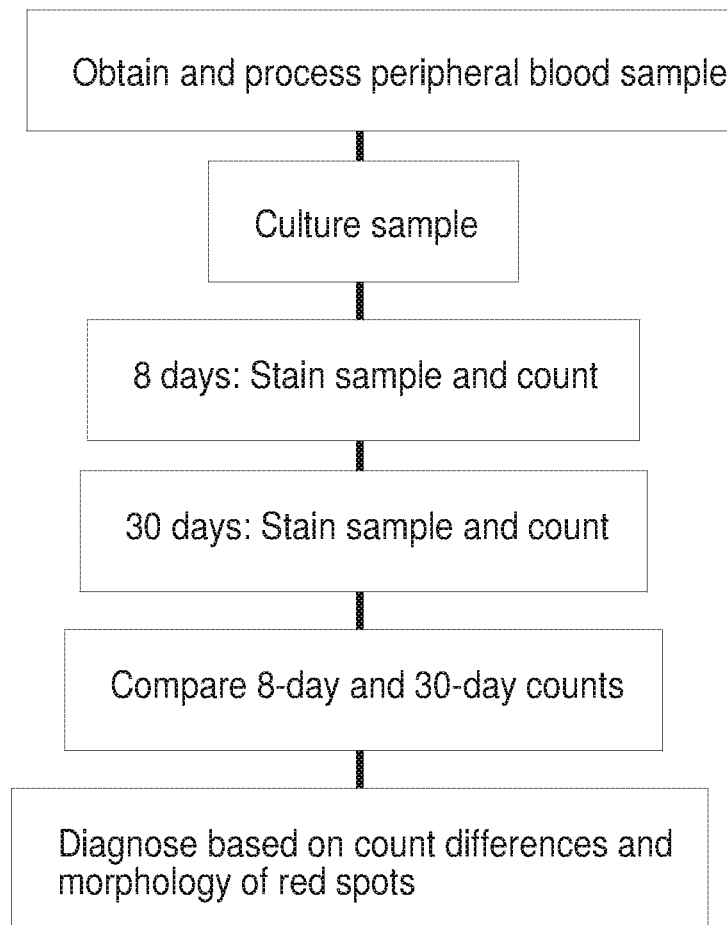
FIG. 1 is a flow chart showing the culturing and staining method of the preferred embodiment

As shown in FIG. 1, the method includes three distinct stages. The first includes preparing a patient sample for culture, and in the second the prepared sample is cultured to selectively stimulate growth of the "red spot" organism. In the third stage, the cultured organism is visualised by fixing a sample including the "red spot" organism to a slide, staining the sample (as will be described below), and visualising the stained sample under ×1000 oil immersion.

The Applicant's research has demonstrated that the 'red spots' visualised using the novel technique are living organisms. The central observations deriving from these investigations, as at the time of this application, are:

- The 'red spots' appear to replicate in liquid and biphasic cultures albeit slowly and with difficulty.
- The 'red spots' are positive for the Ziehl-Neelsen stain (alcohol-free variant).
- The 'red spots' can be cultured onto solid media only with great difficulty.
- The 'red spots' exist with difficulty outside the macrophage.
- The 'red spots' are rapidly taken up by environmental amoebae, and sequestered within the cytoplasm.
- The 'red spots' may be dependent on iron and Mycobactin J.
- The 'red spots' will grow in the presence of non-mycobactericidal antibiotics.
- The 'red spots' are susceptible to specific antimicrobial compounds, both in vivo and in vitro.
- IS900 is not a reliable sequence target for the 'red spots'.
- The 'red spots' can be found in cultures from peripheral blood of patients with multiple sclerosis, type 1 diabetes, IBD (including CD), rheumatoid arthritis and previous BCG immunisation, as well as in some normal controls.

The Applicant has concluded that the "red spots" or "inclusions" visualised by the Applicant's technique are a presumptive Mycobacterium species, and it is probable that they may be spheroplastic forms of MAP or a MAP-like organism.

Figure 2:
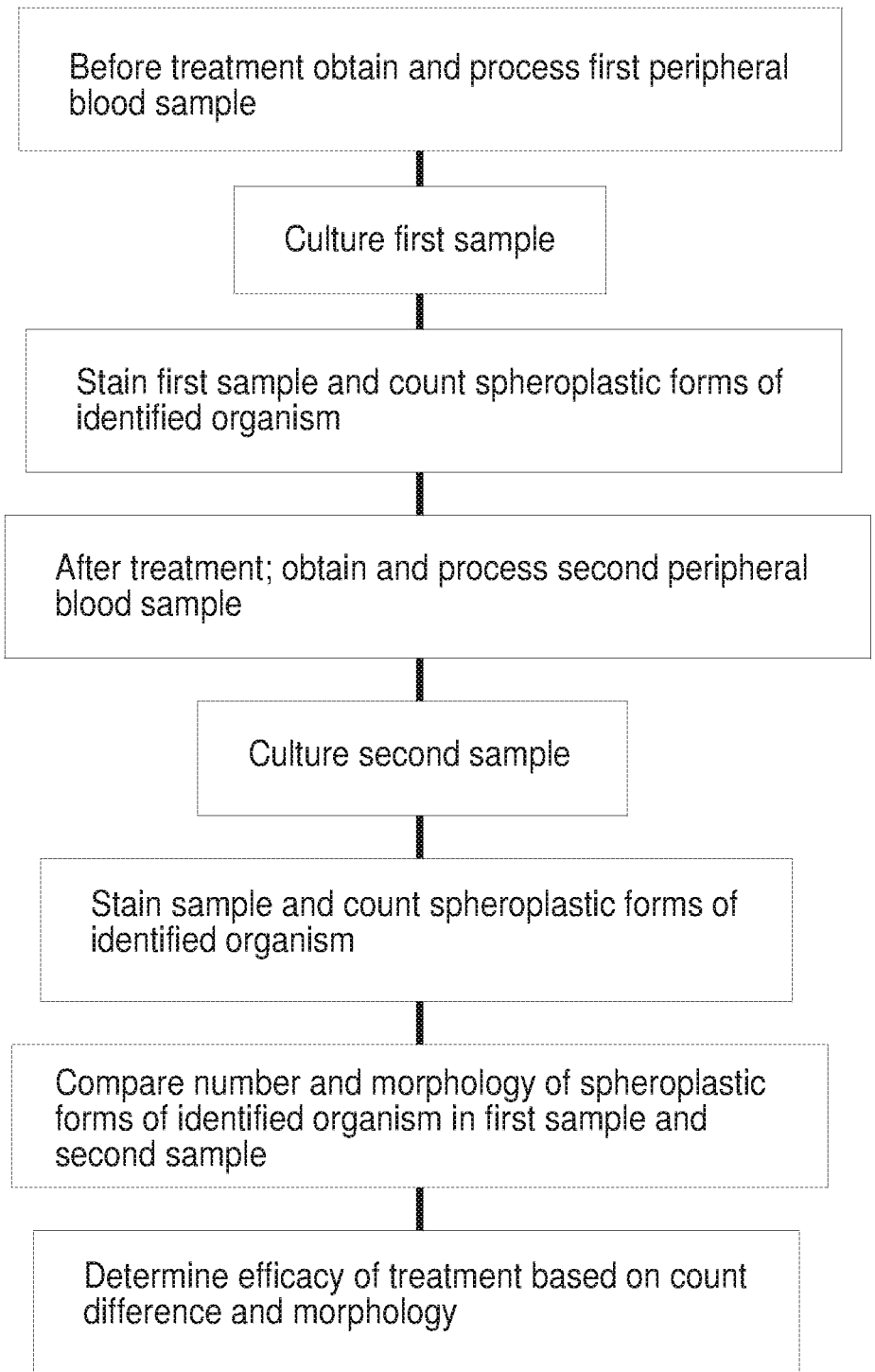
FIG. 2 is a flow chart of a preferred method including a step of determining the efficacy of treatment

The above-described method may be used to assess the effectiveness of treatment being given to a patient, using the method shown in FIG. 2:—before treatment starts, a first blood sample is taken, cultured, stained and the red spots in a sample of the culture are counted. The process is repeated after treatment, and/or at intervals during treatment, and the red-spot counts are compared:—a significant reduction in the number of red spots counted in the samples from the culture indicates that the treatment is effective.

Culture

Spheroplastic forms of the identified organism are difficult to cultivate, as the cell wall is usually absent. Typically, the culture medium must be liquid to mimic the conditions within the macrophage. The present invention provides a method of culturing the organism, such that the organisms are able to be cultured reliably.

The preferred supplemented broth used in the culturing steps includes a mixture of:
- Middlebrook 7H9 broth
- Middlebrook OADC
- PANTA
- mycobactin J
- disaccharide solution.

7H9 broth, OADC, PANTA all are commercially available substances.

The 7H9 broth, the OADC and PANTA additives are made up in known manner, in accordance with the manufacturer's instructions:—the 7H9 broth is prepared by dissolving 4.7 g of the powdered 7H9 medium in 900 mL deionised water and adding 2 mL glycerol.

PANTA contains antimicrobial agents and is supplied as a lyophilized mixture of polymyxin B, amphotericin B, nalidixic acid, trimethoprim and azlocillin, in the relative proportions specified by the manufacturer. PANTA is used in the mixture to exclude potentially contaminating organisms unrelated to the target red spot organism.

The manufacturer supplies PANTA in vials containing the following amounts of the ingredients:
- Polymyxin B—6000 units
- Amphotericin B—600 μg
- Nalidixic acid—2,400 μg
- Trimethoprim—600 μg
- Azlocillin—600 μg The PANTA vial is dissolved in 15 mL of OADC, and the resulting solution is added to the 7H9 broth solution.

OADC is supplied by the manufacturers as a liquid which contains, per litre of purified water:
bovine albumin—50.0 g
dextrose—20.0 g
polyoxyethylene stearate—1.1 g
catalase—0.03 g
oleic acid—0.1 g Mycobactin J is added to the supplemented broth in a proportion of 0.05 mL of mycobactin J to 10 mL of broth.

The disaccharide solution is prepared by dissolving 5 g of sucrose in 5 mL of distilled water, and is added to the supplemented broth in the proportion of 0.2 mL of filtered disaccharide solution to 10 mL of broth.

The proportions of the supplements added to the basic broth may be varied by plus or minus 5%.

The broth is incubated undisturbed in a plastic box containing a water source to provide a humid atmosphere.

At day 8 and at day 30, an aliquot of the sedimented buffy coat (white blood cells) from each tube is withdrawn and spread over the surface of a glass microscope slide. The slide is then heat fixed overnight at approximately 60° C. on a heating plate, and subjected to the staining step described below.

Stain

Previous attempts to visualise what was presumed to be MAP in CD patients (including on tissue, peripheral blood, and breast milk samples) utilised the Ziehl-Neelsen staining method, using alcohol in the method, in particular in the decolouriser. The present method uses a Ziehl-Neelsen staining method in which the decolouriser is alcohol-free and provides an advantage over the prior methods, as the method allows the visualisation of spheroplastic forms of the biomarker.

The spheroplastic form of the biomarker does not have a cell wall, and the stain should not stain the organism unless a cell wall is present. It is therefore surprising to find that the stain, as used in this novel method, is useful in visualising the spheroplastic form of the biomarker.

As described above, after incubation the buffy coat (white blood cells) is harvested and inoculated onto a positive charged microscope slide or equivalent. The slide is air dried and heat fixed. In the Ziehl-Neelsen staining method the slide is laid onto the surface of a heating element and overlaid with Kinyoun Carbol Fuchsin, which is washed off with water. The slide is then overlaid with the decolouriser; in the preferred embodiment the decolouriser is 20% $H_2SO_4$. The slide is again washed with water. The slide is then overlaid with the counterstain, which in the preferred embodiment is 1% methylene blue (in distilled $H_2O$), for one to two minutes and then washed with water. The slide is then dried and examined under ×1000 oil immersion. Cells are counted and the spheroplastic forms are graded as "large", "small", or "ruptured".

In the preferred embodiment $H_2SO_4$ is the decolourising agent, and methylene blue is the counterstain. No alcohol is used in the decolourising agent or in the counterstain.

Figure 3:
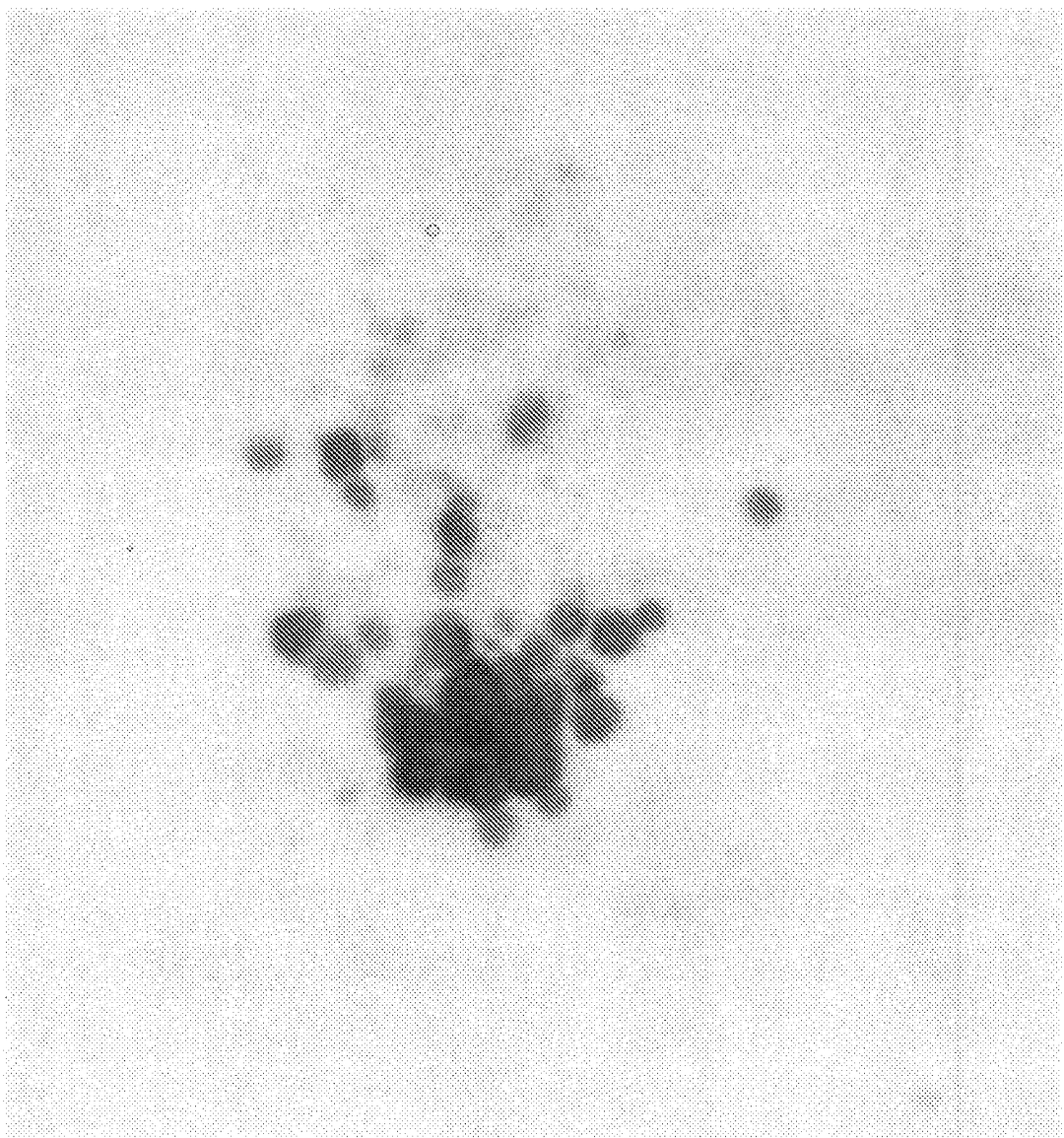
FIG. 3 is a photomicrograph showing spheroplastic forms of the identified organism cultured from a peripheral blood sample of a CD patient and stained after 30 days using the novel method (×1000 oil immersion)

FIG. 3 (photomicrograph) shows spheroplastic forms of the red spot organism cultured from a peripheral blood sample of a CD patient and stained after 30 days incubation using the methods described above. The photomicrograph, which was ×1000 oil immersion, shows well developed substantially circular red spots, some isolated, some of which are developing into clusters.

Figure 4:
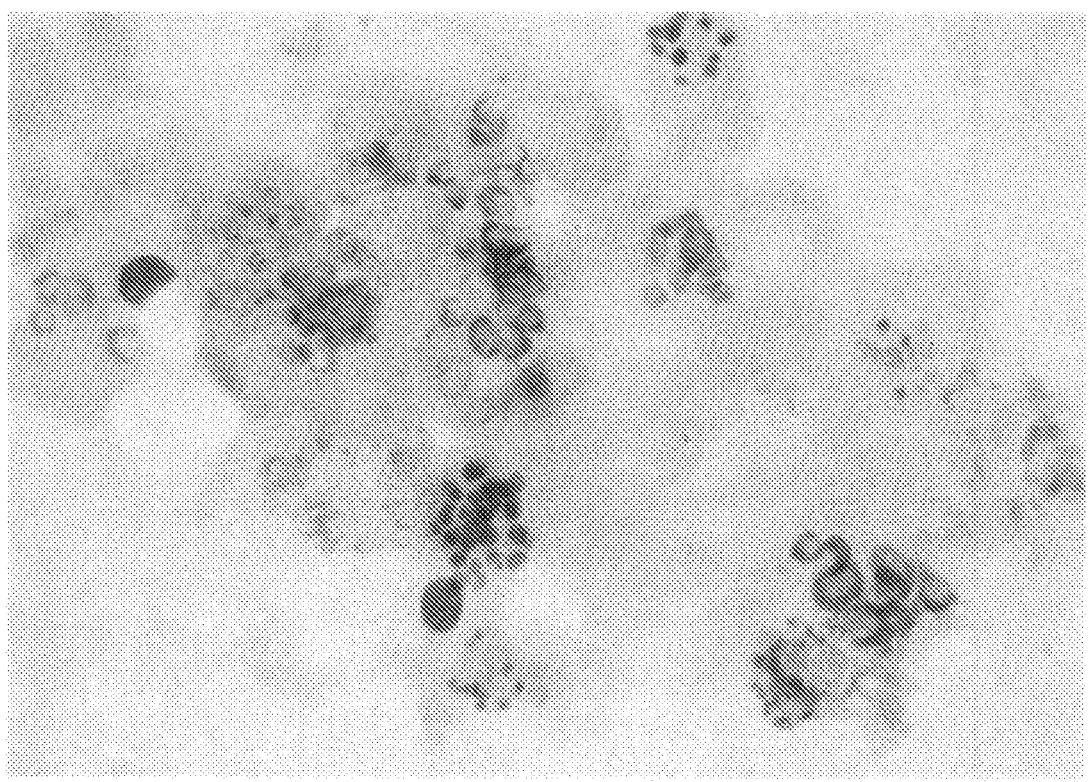
FIG. 4 is a photomicrograph showing rupturing spheroplastic forms of the identified organism cultured from a peripheral blood sample of a CD patient and stained after 30 days using the novel method (×1000 oil immersion) and FIG. 5 is a flow chart of a preferred screening method.

FIG. 4 (photomicrograph) shows rupturing spheroplastic forms of the red spot organism. This photomicrograph also was taken ×1000 oil immersion, again from a culture of a peripheral blood sample of a CD patient, after 30 days incubation using the above described method. However, it will be observed that the defined spheres shown in FIG. 3 are substantially less well defined and show clear signs of rupture.

Diagnosis

The present invention provides a method of diagnosis of inflammatory bowel disease such as CD. The method of the preferred embodiment includes a cultivating step, as previously described. After 8 days a first sample is taken from the culture and subjected to the staining step, as described above, and the number of spheroplastic forms of the identified organism counted and classified. After 30 days a second sample is taken from the culture and subjected to the staining step, as described above, and the number of spheroplastic forms of the identified organism counted and classified. The number and type (i.e. morphology) of spheroplastic forms of the organism in the first sample and the second sample is then compared Using this method, the Applicant correctly diagnosed CD in 64/68 (94%) of CD patients. After 30 days of culture the stained "red spots" had often multiplied to fill the macrophage. In controls 11 out of 12 had low-level staining of red spots at 30 days, with 5 out of 12 correctly identified as normal due to the morphology and sparcity of the spherules.

Diagnosis is achieved by a visual inspection of the stained slide. The number of "red spots", their morphology, and presence/absence of a biofilm are taken into account during diagnosis.

Table 1 shows representative sample results for a patient positive for CD. Overall, the number of "red spots" decreased, ruptured forms decreased, and large forms increased. Media B, C, D, and E are variously supplemented culture broths.

TABLE 1

|  | 8 day Large % | 8 day Small % | 8 day Ruptured % | 30 day Large % | 30 day Small % | 30 day Ruptured % |
| --- | --- | --- | --- | --- | --- | --- |
| Control | 2 | 0 | 65 | 39 | 0 | 3 |
| Media B | 1 | 0 | 52 | 34 | 0 | 0 |
| Media C | 18 | 0 | 27 | 19 | 0 | 8 |
| Media D | 29 | 0 | 16 | 39 | 0 | 24 |
| Media E | 22 | 0 | 40 | 41 | 0 | 30 |

A change in the numbers, such as described above, indicates a viable population of the "red spot" organism in the patient sample.

The present invention also provides an in vitro screening method for:
assessing additives which may promote or inhibit growth of the biomarker during the culturing stage;
assessing the effectiveness of a range of substances which may be used in the treatment of inflammatory bowel disease or Crohn's disease;
evaluating the effectiveness of treatments for inflammatory bowel disease or Crohn's disease.

The object in assessing additives which promote/inhibit growth of the biomarker during the culturing stage is to assist in categorising the biomarker and to assist in identifying the phenotype of the biomarker. Possible growth supplements include a wide range of amino acids and vitamins e.g. Tryptophan glutamine, glutamic acid, vitamin D and the B group including B6, B7, B12, aspartic acid, L asparagine, lysine, arginine, ornithine, cysteine, orotic acid. Possible growth inhibitors include EDTA (Ethylenediamiretetraacetic acid) silver ions, iodine and selenium.

If the biomarker responds in a particular way to any particular additive (e.g. increases its growth rate) then this information assists in categorising the biomarker, because the reaction of the biomarker can be compared to the reactions of known species (in particular known *Mycobacterium* species) to that substance.

Using this screening method also allows possible treatment substances to be tested for the ability to affect the red spot organism in human blood samples, so that further research can be done to determine if that substance will be an effective treatment for inflammatory bowel disease or Crohn's disease patients.

As discussed above, the red spot organism is a presumptive *Mycobacterium* species, possibly MAP or an MAP-like organism. If this assumption is correct, then suitable treatment substances may well be antimicrobial substances, in particular probiotics or antibiotics. Possible substances include clarithromycin, rifabutin, rifampicin, gentamicin, ethambutol, rifaximin, ciprofloxacin, levofloxacin clofazimine.

Figure 5:
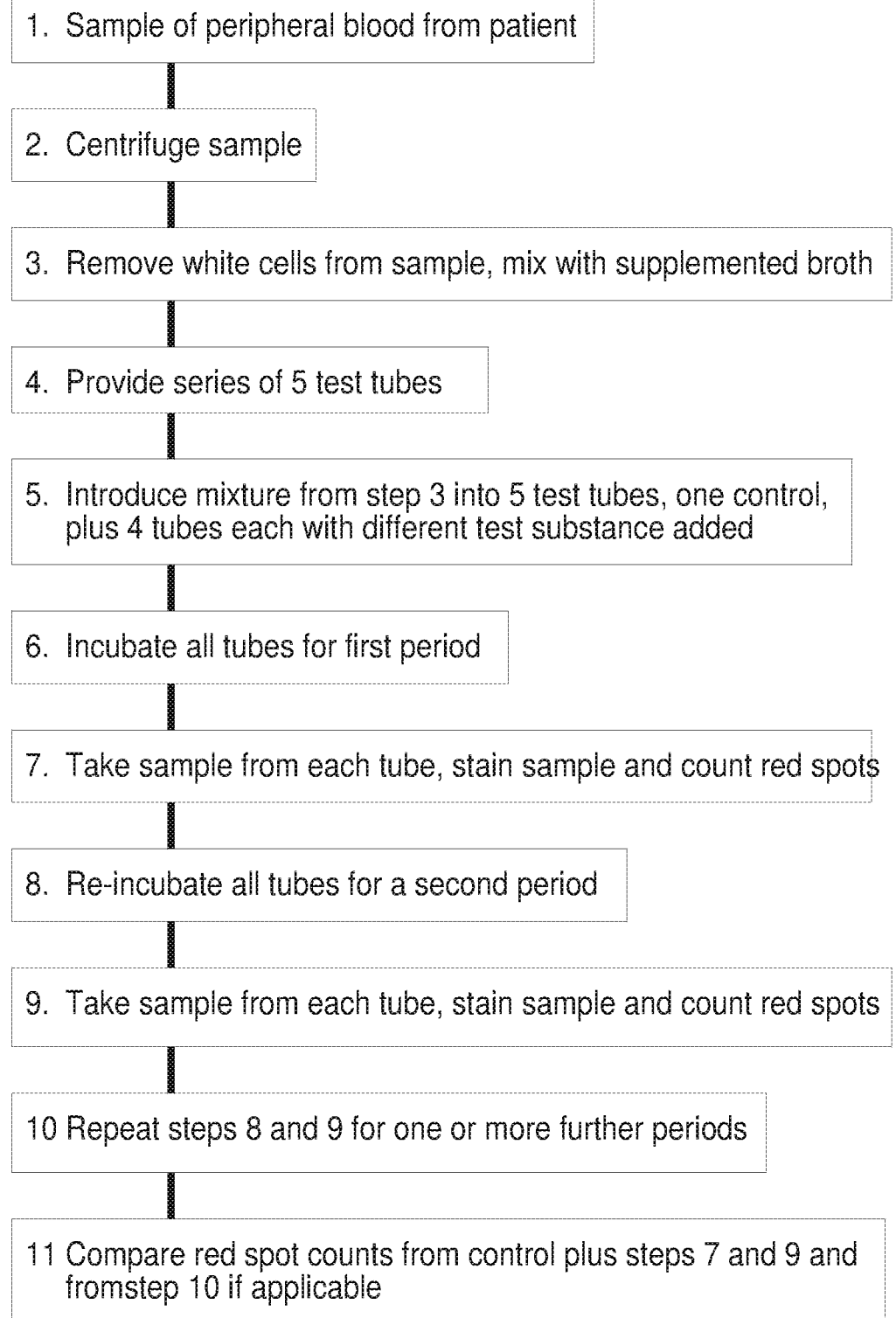

As shown in FIG. 5, the preferred embodiment of this screening method includes the following steps:
1. A sample is taken of the peripheral blood of a patient. Preferably, sodium citrate is used as an anticoagulant.
2. The blood sample is centrifuged for five minutes at 3000 rpm; this tends to move the white blood cells towards the top of the sample.
3. The white cells are removed from the sample using a pipette and mixed into approximately 10 mL of the supplemented broth prepared as described above.
4. A set of five empty sterile bacteriological test tubes is provided, one to act as a control tube, the other 4 to be used to test each of four different substances; 50 µL of each substance to be tested is put in a separate test tube.
5. Between 1.5 and 2 mL of the mixture of white cells and supplemented broth produced in step 3 is placed in each of the five test tubes i.e. one control tube containing only the white cell/supplemented broth mixture and the other four tubes each containing a different substance to be tested plus the white cell/supplemented broth mixture.
6. All of the tubes are then incubated at approximately 37° C. for a first period (e.g. eight days).
7. A sample is then taken from near the bottom of each tube; each sample is stained as described above, using the alcohol free Ziehl Neelsen staining method previously described, and the incidence of red spots in each sample is counted and recorded.
8. The tubes are all then re-incubated at approximately 37° C. for a further 22 days (i.e. 30 days from the start of the test) and then step 7 is repeated.
9. The number and nature of the red spots for each sample is compared between the 8 day sample and the 30 day sample, to see whether the red spots have increased or decreased in number and/or have altered in size or other characteristic.
10. It will be appreciated that the tests may of course be further extended by re-incubating and re-sampling the test solutions over any desired period. The sampling periods of 8 and 30 days have been selected as providing useful results for a majority of test subjects, but these periods may of course be varied as necessary.

When the test results are examined, each test subject is compared with the control and with its own results at each of the sampling periods.

Test subjects may include tests of supplements/additives which can promote or inhibit the growth of the red spot biomarkers. The red spot count observed in a particular test tube can be assessed as an absolute number or as a ratio against the red spot count of the mixture in the control tube. Further, observations on the changing types of red spot biomarkers observed (e.g. size of the red spots observed, or whether the red spots have ruptured or not) can be used as a method to indicate the type of mycobacteria or the strain of mycobacteria which is being observed.

The rate of growth of the mycobacteria in a particular test over the full test period also can be used as an assessment of the severity of the disease and/or the effectiveness of any treatment being given.

If the objective is to test the effectiveness of a treatment being given to the patient, then a blood sample is taken before treatment starts, and the sample is tested as set out above. Further samples are then taken and tested as set out above at intervals during the period of treatment, and the overall results are analysed to see whether the treatment is in fact resulting in a decrease in the incidence of the red spot biomarker; a marked decrease should indicate that the treatment is effective.

These samples may be analysed using the "five tube" method described above or could simply be analysed by taking a first sample from the patient before treatment starts, culturing, sampling and staining this sample as discussed above, and then taking one or more further samples during and/or at the end of treatment, sampling and staining the or each sample, and comparing the number and morphology of the biomarker in the samples.

In general, a small percentage increase or decrease (of the order of up to 3%) is not considered significant. A change of up to 10% may be significant and indicates further study may be advised. A change in the range of 10 to 20% or greater would be considered significant.

TABLE 2

| Patient | Diagnosis | OP test for red spot | PCR test for MAP |
|---|---|---|---|
| 1 | Crohn's | Positive | Positive |
| 2 | Crohn's | Positive | Positive |
| 3 | Crohn's | Positive | Negative |
| 4 | Crohns | Positive | Negative |
| 5 | Crohns | Positive | Positive |
| 6 | Crohns | Positive | Positive |
| 7 | Uncertain ?CD | Equivocal | Negative |
| 8 | Crohn's | Positive | Positive |
| 9 | Resection.nil CD | Positive | Negative |
| 10 | UC | Positive | Positive |
| 11 | Crohn's | Positive | Positive |
| 12 | Crohn's | Equivocal | Positive |
| 13 | Crohn's | Positive | Positive |
| 14 | IBS Neurological | Positive | Positive |
| 15 | Crohn's | Positive | Positive |

Notes

Patient 3 is still under investigation regarding growth.

Patient 7 is still undergoing clinical assessment; may not be Crohns Disease.

Patient 9 had Crohn's disease, but resection of the bowel may have "cured" him. There were organisms isolated but they are not positive for MAP.

Patient 10 has ulcerative colitis.

Patient 12 had an equivocal result from the OP test.

Patient 14 had irritable bowel and a severe ongoing depressive illness.

Patients 1, 4, 5, 6, and 14 were positive for two different probes.

Patients 2, 13, were positive for the F57 probe only.

Patients 8, 10, 11, 12, and 15 were positive for the IS900 probe only.

Table 2 shows a comparative investigation of 15 patients and compares the diagnosis of these patients made by a specialist clinician compared with the "red spot" test in accordance with the present invention ("the OP test") and also with a polymerase chain reaction test ("PCR" test).

The clinician's diagnosis was made on the basis of one or more of: the medical history of the patient; the current symptoms of the patient; a biopsy on the patient.

The OP test was carried out as described above, based on peripheral blood samples taken from each patient; the results were interpreted as "positive" or "negative" by a microbiologist skilled in interpreting the red spot tests. In the Table, "positive" in the OP test column means that red spots were detected in a sufficient number to justify a positive identification of CD; "negative" means that no identification of CD was confirmed.

The PCR test was targeted to detect one or both of the DNA sequences F57 and IS 900, both of which are known to occur in MAP. The PCR test was carried out on the culture of the sample from the patient, rather than specifically the red spots. In the Table, "positive" in the PCR column means that one or both of the target DNA sequences were detected, and MAP was considered to be present; "negative" means that the presence of MAP could not be confirmed.

It will be noted that out of the 15 patients, 10 gave positive results with both the OP test and the PCR test, which also matched the clinical diagnosis. The Notes given below the table give further background information. The test results in Table 2 are interim tests, in that further work is needed to resolve discrepancies, and to finalise the diagnoses.

The high correlation between diagnosis, the OP test and the PCR test lends weight to the postulated link between the presence of MAP and the presence of Crohn's disease.

The invention claimed is:

1. A method of culturing a patient sample in culture media selective for acid-fast mycobacteria, wherein said culture media includes:
   I) a nutrient broth;
   II) Middlebrook OADC liquid containing purified water, bovine albumin, dextrose, catalase and oleic acid;
   III) polyoxyethylene stearate;
   IV) a preparation of polymyxin B, amphotericin B, nalidixic acid, trimethoprim, and azlocillin, in a ratio of 6000 units polymyxin B—:600 µg amphotericin B—:2,400 µg nalidixic acid—:600 µg trimethoprim—:600 µg azlocillin;
   V) ferric mycobactin; and
   VI) at least 0.5% w/v tryptophan.

2. The method of claim 1, wherein said culture media further includes;
   disaccharide solution.

3. The method of claim 1, wherein the nutrient broth is selected from the group consisting of: 7H9, 7H11, Columbia, and Mycobacteria Growth Indicator Tube ('MGIT').

4. The method of claim 1, wherein; said nutrient broth is 7H9 broth, and wherein preparation of the culture media includes
   a) dissolving 4.7 grams of powdered 7H9 medium in 900 mL of deionised water and adding 2 mL of glycerol to prepare the 7H9 broth;
   b) adding 0.2 mL of a sucrose solution for every 10 mL of 7H9 broth;
   c) dissolving the preparation of polymyxin B, amphotericin B, nalidixic acid, trimethoprim, and azlocillin in 15 mL of said Middlebrook OADC and adding the resultant solution to 900 mL of said 7H9 broth; and
   d) adding 0.05 mL of said ferric mycobactin for every 10 mL of the culture media.

5. The method of claim 1, wherein the patient sample is a peripheral blood sample.

6. The method of claim 5, wherein the peripheral blood sample is collected using sodium citrate as an anticoagulant.

7. The method of claim 1, further comprising staining said culture sample using a Ziehl-Neelsen method staining, with an alcohol-free decolouriser.

8. The method of claim 7, wherein said stain is Kinyoun carbol fuchsin.

9. The method of claim 8, wherein said decolouriser is 20% sulphuric acid.

10. The method of claim 9, wherein the Ziehl-Neelsen staining method uses a counterstain consisting of 1% methylene blue in distilled water.

11. A method of culturing and staining acid-fast mycobacteria, said method comprising:
    a) collecting a peripheral blood sample from a patient;
    b) harvesting a buffy coat from the peripheral blood sample;
    c) culturing the harvested buffy coat as claimed in claim 1;
    d) inoculating the cultured buffy coat onto a positively charged carrier;
    e) air drying and heat fixing the carrier and the cultured buffy coat;
    f) placing the carrier on a heating element and overlaying the cultured buffy coat with Kinyoun carbol fuchsin stain;
    g) washing the stain off with water and overlaying the cultured buffy coat with decolouriser in the form of 20% sulphuric acid;
    h) washing the decolouriser off with water and overlaying the cultured buffy coat with counterstain in the form of 1% methylene blue in distilled water for 1-2 minutes;
    i) washing off the counterstain with water;
    j) drying the carrier and the cultured buffy coat.

12. A method of diagnosing inflammatory bowel disease, which includes the following steps:
    a) culturing a patient sample as claimed in claim 1;
    b) taking a first sample from the culture after a first period;
    c) staining the first sample using Ziehl-Neelsen staining method with an alcohol-free decolouriser, so that spheroplastic forms of acid-fast mycobacteria are visualised as red spots;
    d) counting the number of red spots which appear after the staining;
    e) taking a second sample from the culture after a second period which is longer than the first period;
    f) staining the second sample using Ziehl-Neelsen staining method with an alcohol free decolouriser so that spheroplastic forms of acid-fast mycobacteria, are visualised as red spots;
    g) counting the number of red spots which appear after staining;
    h) comparing the number of red spots from the first sample with the number counted from the second sample;
    i) diagnosing inflammatory bowel disease if the number of red spots has increased between the first and second samples.

13. The method of claim 12, wherein the first period is 8 days and the second period is 30 days.

14. The method of claim 12, further comprising comparing the morphology of the red spots in the first sample with the morphology of the red spots in the second sample.

15. A screening method for assessing substances, including:
- a) taking a sample of peripheral blood from a patient;
- b) dividing said blood sample into a plurality of sub-samples, keeping at least one sub-sample as a control, and adding a substance to each of the remaining sub-samples;
- c) inoculating said sub-samples from step b in a culture medium selective for acid-fast mycobacteria, said culture medium including:
  - I) a nutrient broth;
  - II) Middlebrook OADC liquid comprising purified water, bovine albumin, dextrose, catalase and oleic acid;
  - III) polyoxyethylene stearate;
  - IV) a preparation of polymyxin B, amphotericin B, nalidixic acid, trimethoprim, and azlocillin, in a ratio of 6000 units polymyxin B—:600 µg amphotericin B—:2,400 µg nalidixic acid—:600 µg trimethoprim—:600 µg azlocillin;
  - V) ferric mycobactin; and
  - VI) at least 0.5% w/v tryptophan;
- d) incubating said sub-samples in culture medium from step c at a predetermined temperature for a first period;
- e) staining a portion of each sub-sample using a Ziehl-Neelsen staining method with an alcohol-free decolouriser, so that spheroplastic forms of acid-fast mycobacteria are visualised as red spots;
- f) counting and recording the red spots in each Ziehl-Neelsen stained sub sample;
- g) re-incubating said sub-samples from step d at said predetermined temperature for a second period;
- h) repeating steps e and f;
- i) comparing results of step f for each sub-sample after said first and second incubation periods to detect an increase or decrease in the number of red spots in any Ziehl-Neelsen stained sub-sample from said first period to said second period, and
- j) comparing the number of red spots in Ziehl-Neelsen stained sub-samples with substances added, to the number of red spots in the Ziehl-Neelsen stained control sub-sample after said first and second incubation periods, to assess whether said substance has caused an increase or a decrease in the number of red spots.

16. The method of claim 15, wherein between steps a and b, the blood sample is centrifuged so as to concentrate white blood cells in the sample, such that said sub-samples are selected from the portion of the sample where the white blood cells are concentrated.

17. The method of claim 15, wherein in step f, morphology of the red spots in each sample also is recorded.

18. The method of claim 15, wherein said predetermined temperature is 37 degrees centigrade, said first period is 8 days and said second period is 30 days.

19. The method of claim 15, wherein the substances to be assessed are substances for treating inflammatory bowel disease and/or Crohn's disease.

20. The method of claim 19, wherein the substances to be assessed are selected from the group consisting of: clarithromycin, rifabutin, rifampicin, gentamicin, ethambutol, rifaximin, ciprofloxacin, levofloxacin and clofazimine.

21. The method of claim 15, wherein the substances are selected from the group consisting of: glutamine, glutamic acid, vitamin D, vitamin B1, vitamin B2, vitamin B3, vitamin B5, vitamin B6, vitamin B7, vitamin B9, vitamin B12, aspartic acid, L asparagine, lysine, arginine, ornithine, cysteine, orotic acid, Ethylenediamiretetraacetic acid (EDTA), silver ions, iodine and selenium.

22. A screening method for assessing effectiveness of a treatment of a patient, said method including the steps of:
- a) taking a preliminary blood sample from the patient before treatment;
- b) treating the patient;
- c) taking blood samples from the patient at intervals during the treatment and/or at the end of treatment;
- d) inoculating said preliminary blood sample and each of the blood samples from step c in a culture medium selective for acid-fast mycobacteria, said culture medium including:
  - I) a nutrient broth;
  - II) Middlebrook OADC liquid comprising purified water, bovine albumin, dextrose, catalase and oleic acid;
  - III) polyoxyethylene stearate;
  - IV) a preparation of polymyxin B, amphotericin B, nalidixic acid, trimethoprim, and azlocillin, in a ratio of 6000 units polymyxin B—:600 µg amphotericin B—:2,400 µg nalidixic acid—:600 µg trimethoprim—:600 µg azlocillin;
  - V) ferric mycobactin; and
  - VI) at least 0.5% w/v tryptophan;
- e) incubating each sample from step d at a predetermined temperature for a predetermined period, to culture each sample;
- f) staining each cultured sample after step e using a Ziehl-Neelsen staining method with an alcohol-free decolouriser, so that spheroplastic forms of acid-fast mycobacteria are visualised as red spots;
- g) counting and recording the red spots in each Ziehl-Neelsen stained sample, to detect a significant decrease in the number of red spots as a result of said treatment.

23. The method of claim 22, wherein the treatment is a treatment for inflammatory bowel disease.

* * * * *